US012263035B2

(12) United States Patent
Stigall et al.

(10) Patent No.: US 12,263,035 B2
(45) Date of Patent: Apr. 1, 2025

(54) DIRECTIONAL MARKERS FOR INTRALUMINAL IMAGING DEVICE

(71) Applicant: KONINKLIJKE PHILIPS N.V., Eindhoven (NL)

(72) Inventors: Jeremy Stigall, Carlsbad, CA (US); Maritess Minas, San Diego, CA (US); Nathan Andrew Williams, San Diego, CA (US); Annamarie Mendoza-Cruz, San Diego, CA (US); Princeton Saroha, Ladera Ranch, CA (US); David Kenneth Wrolstad, Fallbrook, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 616 days.

(21) Appl. No.: 16/497,467

(22) PCT Filed: Mar. 26, 2018

(86) PCT No.: PCT/EP2018/057596
§ 371 (c)(1),
(2) Date: Sep. 25, 2019

(87) PCT Pub. No.: WO2018/177983
PCT Pub. Date: Oct. 4, 2018

(65) Prior Publication Data
US 2021/0106308 A1    Apr. 15, 2021

Related U.S. Application Data

(60) Provisional application No. 62/478,776, filed on Mar. 30, 2017.

(51) Int. Cl.
*A61B 8/12*    (2006.01)
*A61B 8/00*    (2006.01)
*A61B 90/00*   (2016.01)

(52) U.S. Cl.
CPC ............... *A61B 8/12* (2013.01); *A61B 8/445* (2013.01); *A61B 90/39* (2016.02); *A61B 2090/3966* (2016.02)

(58) Field of Classification Search
None
See application file for complete search history.

(56) References Cited

U.S. PATENT DOCUMENTS 5,203,777 A    4/1993  Lee
6,285,903 B1   9/2001  Rosenthal
(Continued)

FOREIGN PATENT DOCUMENTS

WO    2010092512 A1    8/2010

OTHER PUBLICATIONS

International Search Report & Written Opinion of PCT/EP2018/057596, dated Jul. 16, 2018.

*Primary Examiner* — Shahdeep Mohammed

(57) ABSTRACT

An intraluminal device is provided. In on embodiment, an intraluminal device includes a flexible elongate member including a proximal portion and a distal portion; an imaging component coupled to the distal portion of the flexible elongate member; and a plurality of radiopaque markers positioned at the distal portion of the flexible elongate member, wherein the plurality of radiopaque markers are separated from each other, wherein the plurality of radiopaque markers are arranged on the flexible elongate member at two different orientations with respect to the imaging component, and wherein at least a first radiopaque marker of the plurality of radiopaque markers includes an arc-shaped portion and an extended portion extending from the arc-shaped portion.

12 Claims, 12 Drawing Sheets

(56) References Cited

U.S. PATENT DOCUMENTS

| | | |
|---|---|---|
| 6,520,934 B1 | 2/2003 | Lee |
| 7,846,101 B2 | 12/2010 | Eberle |
| 2003/0167052 A1 | 9/2003 | Lee |
| 2005/0064224 A1* | 3/2005 | Bavaro ............ A61M 25/1027 |
| | | 252/515 |
| 2005/0133941 A1 | 6/2005 | Schuhmacher |
| 2013/0197353 A1* | 8/2013 | Von Oepen ....... A61M 25/0009 |
| | | 29/2.25 |
| 2014/0180068 A1 | 6/2014 | Spencer |
| 2016/0045219 A1* | 2/2016 | Guala ................ A61B 17/3478 |
| | | 606/185 |
| 2016/0303348 A1* | 10/2016 | Leung ............... A61M 25/0108 |
| 2017/0050000 A1* | 2/2017 | Randall ................ A61M 25/04 |
| 2017/0100141 A1* | 4/2017 | Morero ............ A61M 25/0194 |

* cited by examiner

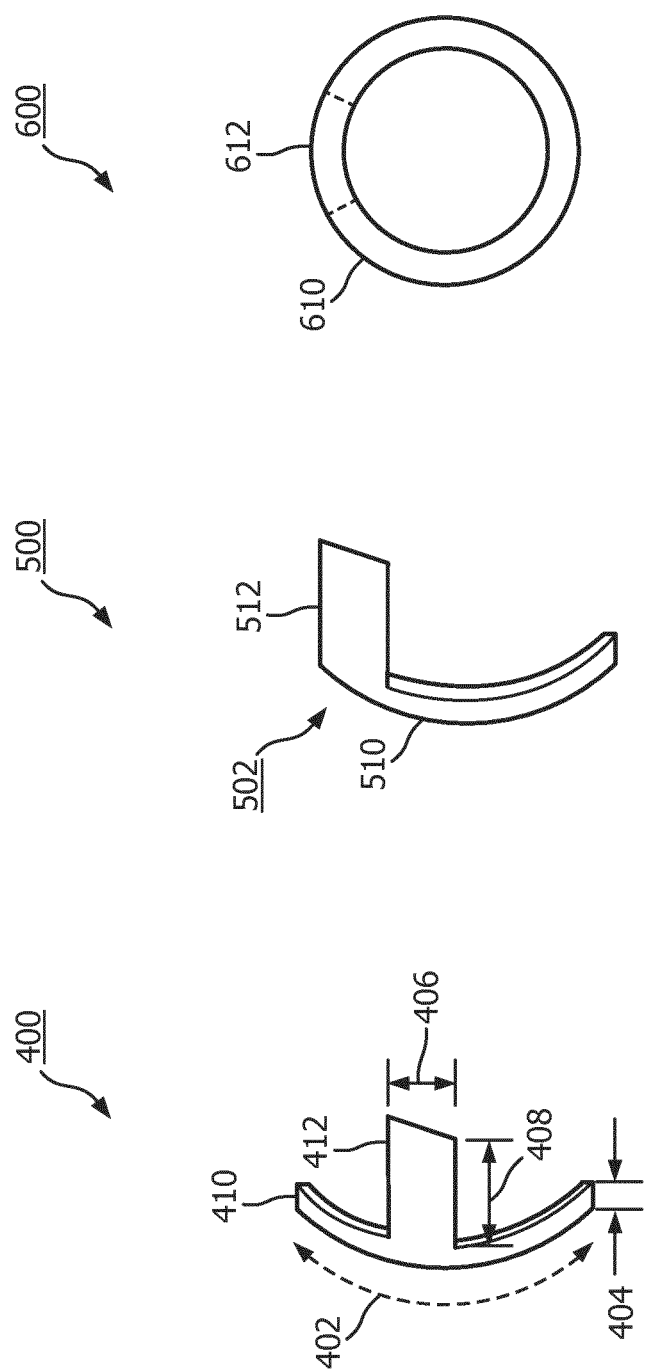

DIRECTIONAL MARKERS FOR INTRALUMINAL IMAGING DEVICE

RELATED APPLICATION

This invention claims the benefit of and priority to U.S. Provisional No. 62/478,776, filed Mar. 30, 2017, which is incorporated by reference in its entirety.

TECHNICAL FIELD

The present disclosure relates generally to intraluminal devices, in particular, to providing directional guidance during intraluminal procedures as to length, orientation, and distance to a target treatment site or imaging site. For example, a catheter assembly can include radiopaque markers staggered in a particular pattern with respect to an orientation of the imaging device or treatment device.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

There are two types of IVUS catheters commonly in use today: rotational and solid-state. For a typical rotational IVUS catheter, a single ultrasound transducer element is located at the tip of a flexible driveshaft that spins inside a plastic sheath inserted into the vessel of interest. The transducer element is oriented such that the ultrasound beam propagates generally perpendicular to the axis of the device. The fluid-filled sheath protects the vessel tissue from the spinning transducer and driveshaft while permitting ultrasound signals to propagate from the transducer into the tissue and back. As the driveshaft rotates, the transducer is periodically excited with a high voltage pulse to emit a short burst of ultrasound. The same transducer then listens for the returning echoes reflected from various tissue structures. The IVUS imaging system assembles a two dimensional display of the vessel cross-section from a sequence of pulse/acquisition cycles occurring during a single revolution of the transducer.

Solid-state IVUS catheters carry a sensing assembly or scanner assembly that includes an array of ultrasound transducers distributed around its circumference along with one or more integrated circuit controller chips mounted adjacent to the transducer array. The solid-state IVUS catheters are also referred to as phased array IVUS transducers. The controllers select individual transducer elements (or groups of elements) for transmitting an ultrasound pulse and for receiving the ultrasound echo signal. By stepping through a sequence of transmit-receive pairs, the solid-state IVUS system can synthesize the effect of a mechanically scanned ultrasound transducer but without moving parts (hence the solid-state designation). Since there is no rotating mechanical element, the transducer array can be placed in direct contact with the blood and vessel tissue with minimal risk of vessel trauma. Furthermore, because there is no rotating element, the electrical interface is simplified. The solid-state scanner can be wired directly to the imaging system with a simple electrical cable and a standard detachable electrical connector, rather than the complex rotating electrical interface required for a rotational IVUS device.

While phased array IVUS devices are often used in conjunction with other intraluminal treatment devices to provide guidance during vasculature procedures, the circumferential firing sequence of the transmit-receive pairs needs to be correlated to the target site, for example, the orientations of the imaging, to compile useful image data for the vasculature procedures.

SUMMARY

Embodiments of the present disclosure provide improved intraluminal devices with rotational or axial directional guidance for accessing human vasculatures. For example, an intraluminal device can include a flexible elongate member for accessing coronary anatomy or remote tortuous vascular regions. The flexible elongate member can include an imaging component such as phased array transducers for internal imaging and a medical treatment component for treatment (e.g., atherectomy). The disclosed embodiments provide directional or rotational guidance with respect to the axial positioning of the intraluminal device by including a series of individual radiopaque markers spaced apart on the flexible elongate member, for example, between an inner tubular member and an outer tubular member of the flexible elongate member. The geometries of the radiopaque markers and/or the positioning of the radiopaque markers are configured to provide different patterns as the flexible elongate member is rotated about the longitudinal axis and viewed axially. In an embodiment, the radiopaque markers are can have a T-shape or an L-shape, where the T-shapes and/or the L-shapes are arranged in a staggered pattern on the flexible elongate member. As such, external imaging (e.g., X-ray fluoroscopy) can be used to image the radiopaque markers and the axial position can be defined based on the specific arrangement or pattern of the radiopaque markers captured in the image.

Various manufacturing methods can be used to assemble an intraluminal device with directional radiopaque markers. In one embodiment, the radiopaque markers can be thermally bonded to an outer wall of the inner tubular member and/or an outer wall of the outer tubular member using a tackweld process. In another embodiment, the directional markers can be swaged onto the outer wall of the inner tubular member. In yet another embodiment, the directional markers can be in the form of radiopaque coils attached to a flexible wire.

In one embodiment, an intraluminal device is provided. The intraluminal device includes a flexible elongate member including a proximal portion and a distal portion; an imaging component coupled to the distal portion of the flexible elongate member; and a plurality of radiopaque markers positioned at the distal portion of the flexible elongate member, wherein the plurality of radiopaque markers are separated from each other, wherein the plurality of radiopaque markers are arranged on the flexible elongate member at two different orientations with respect to the imaging component, and wherein at least a first radiopaque marker of the plurality of radiopaque markers includes an arc-shaped portion and an extended portion extending from the arc-shaped portion.

In some embodiments, the arc-shaped portion and the extended portion of the first radiopaque marker forms a T-shape. In some embodiments, the arc-shaped portion and the extended portion of the first radiopaque marker forms an L-shape. In some embodiments, the plurality of radiopaque markers comprises different arrangement patterns comprising at least one of different shapes, different sizes, or different distances to adjacent radiopaque markers. In some embodiments, each of the plurality of radiopaque markers includes an arc-shaped portion and an extended portion extending from the arc-shaped portion, and wherein at least the extended portions or the arc-shaped portions are offset from each other. In some embodiments, the flexible elongate member includes an inner tubular member and an outer tubular member extending between the proximal portion and the distal portion, and wherein the plurality of radiopaque markers is positioned between the inner tubular member and the outer tubular member at the distal portion. In some embodiments, the arc-shaped portion of the first radiopaque marker is positioned around a portion of an outer diameter of the inner tubular member, and wherein the extended portion of the first radiopaque marker extends along an outer wall of the inner tubular member. In some embodiments, at least portions of the plurality of the radiopaque markers are thermally bonded to at least an outer wall of the inner tubular member. In some embodiments, at least portions of the plurality of the radiopaque markers are thermally bonded to an outer wall of the inner tubular member and an inner wall of the outer tubular member. In some embodiments, the plurality of the radiopaque markers is swaged onto at least an outer wall of the inner tubular member by an adhesive. In some embodiments, the plurality of the radiopaque markers is bonded to at least an outer wall of the inner tubular member by an adhesive. In some embodiments, the plurality of the radiopaque markers includes at least one of a tungsten material, platinum, or iridium.

In one embodiment, an intraluminal device is provided. The intraluminal device includes a flexible elongate member including a proximal portion and a distal portion; an imaging component coupled to the distal portion of the flexible elongate member; and a plurality of radiopaque markers positioned at the distal portion of the flexible elongate member, wherein the plurality of radiopaque markers are spaced from each other, wherein the plurality of radiopaque markers are arranged on the flexible elongate member at two different orientations with respect to the imaging component, and wherein the plurality of radiopaque markers is attached to a flexible element extending along the flexible elongate member.

In some embodiments, the flexible elongate member includes an inner tubular member and an outer tubular member extending between the proximal portion and the distal portion, and wherein the plurality of radiopaque markers is positioned between the inner tubular member and the outer tubular member at the distal portion. In some embodiments, the flexible element is bonded to an outer wall of the inner tubular member by an adhesive. In some embodiments, the flexible element is a wire extending along a length between the inner tubular member and the outer tubular member. In some embodiments, at least a first radiopaque marker of the plurality of radiopaque markers includes an arc-shaped portion and an extended portion extending from the arc-shaped portion. In some embodiments, each of the plurality of radiopaque markers includes an arc-shaped portion and an extended portion extending from the arc-shaped portion, and wherein at least the extended portions or the arc-shaped portions of the plurality of radiopaque markers are offset from each other. In some embodiments, the plurality of radiopaque markers comprises a plurality of radiopaque coils.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 4 is a diagrammatic perspective view of a directional marker, according to aspects of the present disclosure.

FIG. 5 is a diagrammatic perspective view of a directional marker, according to aspects of the present disclosure.

FIG. 6 is a diagrammatic perspective view of a directional marker, according to aspects of the present disclosure.

DETAILED DESCRIPTION

Figure 1:
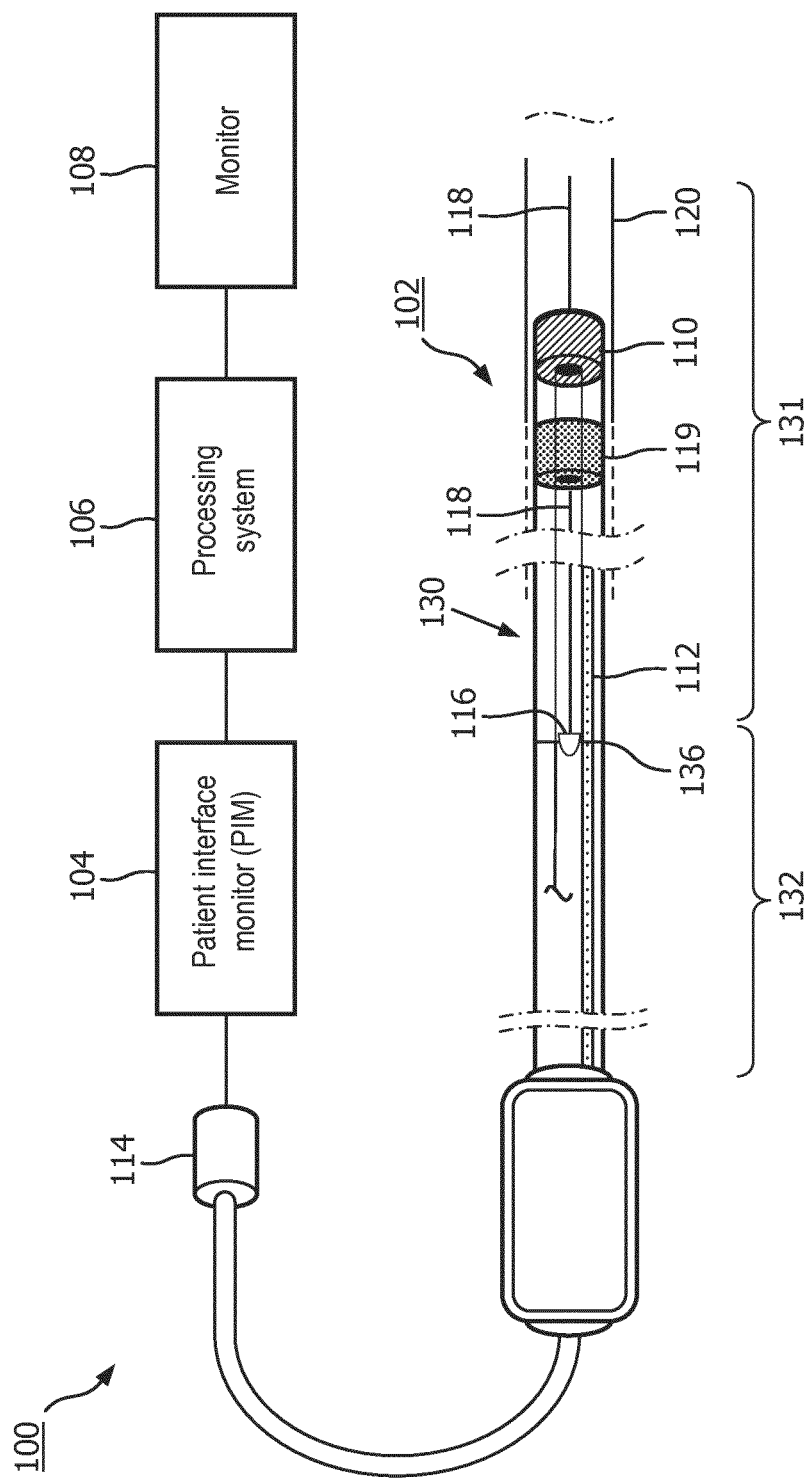
FIG. 1 is a diagrammatic schematic view of an intraluminal system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an intraluminal system 100, according to aspects of the present disclosure. The system 100 may include an intraluminal device 102 such as a catheter, guide wire, or guide catheter, a patient interface module (PIM) 104, a processing system 106, such as a console and/or a computer, and a monitor 108.

In some embodiments, the intraluminal device 102 may be an imaging device, such as an IVUS imaging device. The intraluminal device 102 may include an imaging assembly 110 mounted at a distal portion 131 near a distal end of the intraluminal device 102. At a high level, the intraluminal device 102 emits ultrasonic energy from a transducer array included in the imaging assembly 110. The ultrasonic energy is reflected by tissue structures in the medium, such as a vessel 120, surrounding the imaging assembly 110, and the ultrasound echo signals are received by the transducer array in the imaging assembly 110. Although the imaging assembly 110 is illustrated with a configuration for a transducer array, the imaging assembly 110 may be alternatively configured to include a rotational transducer to achieve similar functionalities. The PIM 104 transfers the received echo signals to the processing system 106 where the ultrasound image (including the flow information) is reconstructed and displayed on the monitor 108. The processing system 106 can include a processor and a memory. The processing system 106 can be operable to facilitate the features of the system 100 described herein. For example, the processor can execute computer readable instructions stored on the non-transitory tangible computer readable medium.

In some embodiments, the intraluminal device 102 may include a medical treatment assembly 119 configured to remove atherosclerotic or calcified plaque. For example, the medical treatment assembly 119 can be a plaque excision atherectomy device, a rotational atherectomy device, a laser atheroablation device, or an orbital atherectomy device. In other embodiments, the assembly 119 can include any suitable treatment device, such as an ablation device, stent, etc. The imaging assembly 110 can be used in conjunction with the medical treatment assembly 119 to obtained images to guide a medical treatment procedure, for example, before, during, and/or after the medical treatment procedure.

In some other embodiments, the medical treatment assembly 119 is configured to sense and obtain physiologic data associated with pressure, flow, temperature, forward looking IVUS (FL-IVUS), intravascular photoacoustic (IVPA) imaging, a fractional flow reserve (FFR) determination, a functional measurement determination, a coronary flow reserve (CFR) determination, optical coherence tomography (OCT), computed tomography, intracardiac echocardiography (ICE), forward-looking ICE (FLICE), intravascular palpography, transesophageal ultrasound, and/or other suitable types of physiologic data.

The PIM 104 facilitates communication of signals between the processing system 106 and the imaging assembly 110 and/or the medical treatment assembly 119 included in the intraluminal device 102. In some embodiments, the PIM 104 performs preliminary processing of the echo data prior to relaying the data to the processing system 106. In examples of such embodiments, the PIM 104 performs amplification, filtering, and/or aggregating of the data. In an embodiment, the PIM 104 also supplies high- and low-voltage direct current (DC) power to support operation of the device 102 including circuitry within the imaging assembly 110 and the medical treatment assembly 119.

The processing system 106 receives the echo data from the imaging assembly 110 by way of the PIM 104 and processes the data to reconstruct an image of the tissue structures in the medium surrounding imaging assembly 110. The processing system 106 outputs image data such that an image of a vessel, such as a cross-sectional image of the vessel 120, is displayed on the monitor 108. The vessel 120 may represent fluid filled or surrounded structures, both natural and man-made. The vessel 120 may be within a body of a patient. The vessel 120 may be a blood vessel, as an artery or a vein of a patient's vascular system, including cardiac vasculature, peripheral vasculature, neural vasculature, renal vasculature, and/or or any other suitable lumen inside the body. For example, the intraluminal device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the intraluminal device 102 may be used to examine man-made structures such as, but without limitation, heart valves, stents, shunts, filters and other devices.

In some embodiments, the intraluminal device 102 includes some features similar to traditional solid-state IVUS catheters, such as the EagleEye® catheter available from Volcano Corporation and those disclosed in U.S. Pat. No. 7,846,101 hereby incorporated by reference in its entirety. For example, the intraluminal device 102 includes the imaging assembly 110 near a distal end of the intraluminal device 102 and an electrical cable 112 extending along the longitudinal body of the intraluminal device 102. The cable 112 is a transmission line bundle including a plurality of conductors, including one, two, three, four, five, six, seven, or more conductors. It is understood that any suitable gauge wire can be used for the conductors. In an embodiment, the cable 112 can include a four-conductor transmission line arrangement with, e.g., 41 American wire gauge (AWG) wires. In an embodiment, the cable 112 can include a seven-conductor transmission line arrangement utilizing, e.g., 44 AWG wires. In some embodiments, 43 AWG wires can be used.

The cable 112 terminates in a PIM connector 114 at a proximal end of the intraluminal device 102. The PIM connector 114 electrically couples the cable 112 to the PIM 104 and physically couples the intraluminal device 102 to the PIM 104. In an embodiment, the intraluminal device 102 further includes a guide wire exit port 116 disposed near a junction 130 at which a distal portion 131 is coupled to a proximal portion 132. Accordingly, in some instances the IVUS device is a rapid-exchange catheter. The guide wire exit port 116 allows a guide wire 118 to be inserted towards the distal end in order to direct the intraluminal device 102 through the vessel 120.

Figure 2:
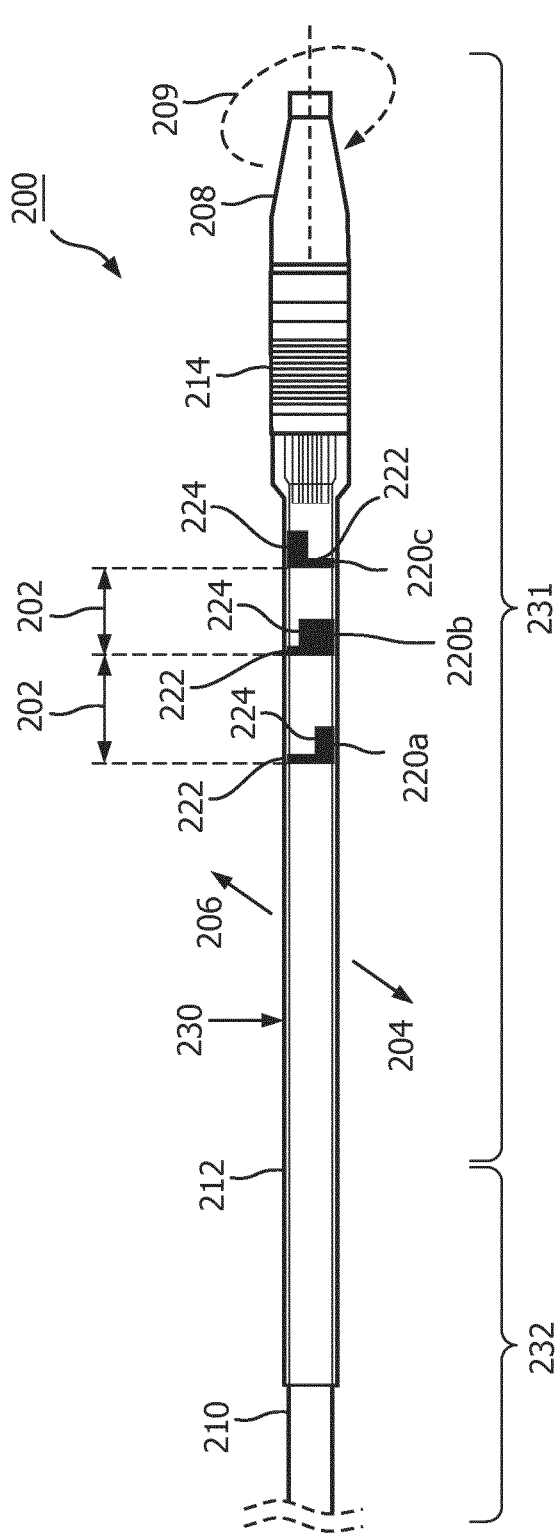
FIG. 2 is a diagrammatic side view of a portion of an intraluminal device with directional markers, according to aspects of the present disclosure.

FIG. 2 is a diagrammatic side view of a portion of an intraluminal device 200 with directional markers 220, according to aspects of the present disclosure. The intraluminal device 200 is similar to the intraluminal device 102 and can be used in the system 100 in place of the intraluminal device 102. The intraluminal device 200 includes a flexible elongate member 230, an imaging component 214, and the directional markers 220. The flexible elongate member 230 includes a distal portion 231 and a proximal portion 232. The flexible elongate member 230 can be composed of any suitable material, such as Pebax® polyether block amides. The flexible elongate member 230 can be fabricated by conventional extrusion techniques or any suitable techniques. The flexible elongate member 230 includes an inner tubular member 210 and an outer tubular member 212 extending between the distal portion 231 and the proximal portion 232. The inner tubular member 210 can include a lumen (not shown) extending along a length of the inner tubular member 210. The lumen can be sized and shaped to accommodate an electrical cable, such as the electrical cable 112, for transferring image signals from the imaging component 214 to an external processing system, such as the processing system 106. The imaging component 214 is similar to the imaging assembly 110. The imaging component 214 is positioned at the distal portion 231 of the flexible elongate member 230.

The directional markers 220 are individual markers positioned at the distal portion 231 of the flexible elongate member 230 proximal to the imaging component 214. In some embodiments, when the intraluminal device 200 includes other medical treatment assembly, such as the medical treatment assembly 119, the directional markers 220 can be positioned proximal to the medical treatment assembly. In an embodiment, the directional markers 220 are positioned between the inner tubular member 210 and the outer tubular member 212. The assembling of the directional markers 220 with the intraluminal device 200 is described in greater detail herein.

The directional markers 220 are radiopaque markers including materials such as tungsten, platinum, iridium, and/or any suitable radiopaque material. The use of the radiopaque material allows the directional markers 220 to be imaged by external imaging, such as X-ray fluoroscopy or magnetic resonance imaging (MRI). The directional markers 220 can be configured with different shapes and/or sizes and arranged on the flexible elongate member 230 such that the directional markers 220 provide different visual patterns on the flexible elongate member 230 at different rotational angles when viewed axially. For example, the directional markers 220 can be positioned at two or more different orientations with respect to the imaging component 214. As such, the directional markers 220 can be used to determine a directional and/or rotational orientation of the imaging component 214 and/or other medical treatment devices (e.g., the medical treatment assembly 119) on the intraluminal device 200 with respect to a target site when under external imaging.

As shown, each directional marker 220 has a half circle band 222 and an extended portion 224 extending from the half circle band 222. The extended portions 224 of the directional markers 220 can have different sizes as shown or the same size. In some other embodiments, the directional marker 220 can have other shapes and/or sizes, as described in greater detail herein. The directional markers 220 separate markers spaced apart from each other by a distance 202 and are positioned such that the extended portions 224 are offset from each other forming a staggered pattern on a side 204 (e.g., at a particular angle) of the intraluminal device 200. The distance 202 can vary depending on the embodiments. In some particular embodiments, the distance 202 can be between approximately 5 millimeters (mm) and approximately 15 mm, including values such as 10 mm.

Figure 3:
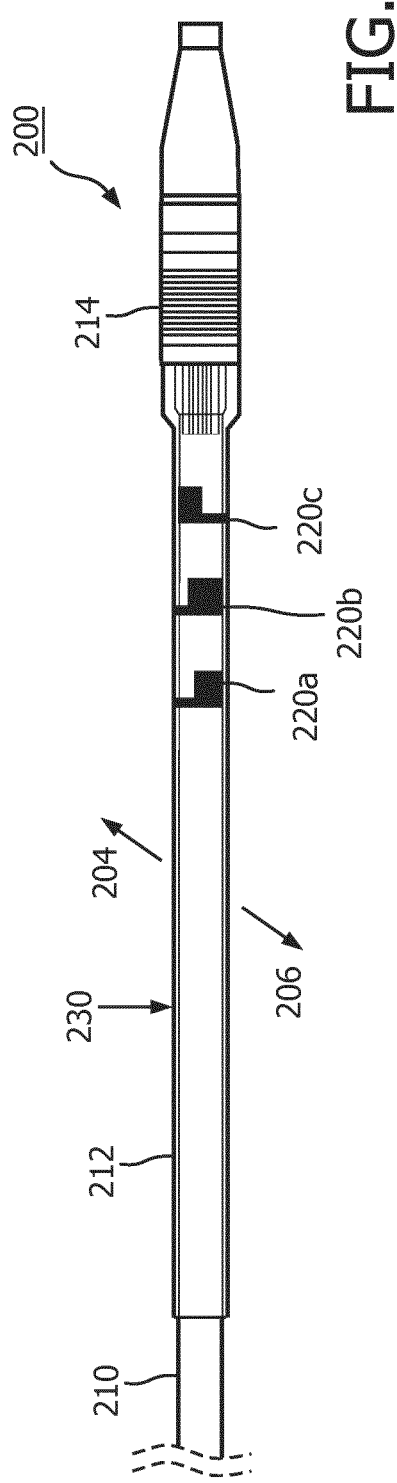
FIG. 3 is a diagrammatic side view of a portion of an intraluminal device with directional markers, according to aspects of the present disclosure.

FIG. 3 is a diagrammatic side view of a portion of the intraluminal device 200 with the directional markers 220, according to aspects of the present disclosure. FIG. 3 illustrates the intraluminal device 200 viewing from a side 206 of the flexible elongate member 230 opposite the side 204. For example, FIG. 3 is obtained by rotating the intraluminal device 200 of FIG. 2 about the longitudinal axis 208 by about 180 degrees as shown by the arrow 209 of FIG. 2. As shown, the directional markers 220 are on the side 204, and thus the directional markers 220 cannot be seen when imaging from the side 206. In an embodiment, the imaging component 214 can be positioned on the flexible elongate member 230 such that the transducer array emits ultrasound signals from the side 204. As such, during an intravascular procedure, an external imaging system (e.g., X-ray fluoroscopy) can be used to obtain images of the directional markers 220 on the intraluminal device 200 and the orientation of the imaging component 214 can be determined based on the images.

For example, when an image captures the directional markers 220 as viewed in FIG. 2, a clinician can determine that the signal emitting side of the imaging component 214 is pointing towards the imaging plane of the external imaging system. Alternatively, when an image captures the side 206 with no directional marker 220 as viewed in FIG. 3, a clinician can determine that the signal emitting side of the imaging component 214 is pointing away from the imaging plane of the external imaging system. Thus, the directional markers 220 can be arranged such that the directional markers 220 form different patterns with respect to different orientations of the imaging component 214 or the medical treatment device to provide directional guidance during a medical treatment procedure. For example, external imaging can be used to capture the directional markers 220 and internal imaging via the imaging component 214 can be used to capture a target site. Information obtained from the external image captures and the internal image captures can be combined or correlated to provide directional and/or rotational information regarding relative positions between the imaging component 214 or the medical treatment device and the target site. While FIGS. 2 and 3 illustrate three directional markers 220 with the half circle bands 222 aligned to one another, the half circle bands 222 can be offset from each other in addition to the extended portions 224 to provide a finer orientation granularity (e.g., angle granularity). In addition, the intraluminal device 200 can include any suitable number of directional markers.

FIGS. 4, 5, and 6 illustrate example geometric configurations of directional radiopaque markers that can be used in the intraluminal device 200 in place of any of the directional markers 220. FIG. 4 is a diagrammatic perspective view of a directional marker 400, according to aspects of the present disclosure. The directional marker 400 is a radiopaque marker similar to the directional marker 220*b*. As shown, the directional marker 400 includes an arc-shaped portion 410 and an extended portion 412 extending from the arc-shaped portion 410. For example, the extended portion 412 can be about perpendicular to the arc-shaped portion 410. When the directional marker 400 is positioned on the intraluminal device 200, the arc-shaped portion 410 wraps around a portion of an outer diameter of the inner tubular member 210 and the extended portion 412 extends along an outer surface of the inner tubular member 210. In an embodiment, the directional marker 400 can be affixed to a ring for assembly purpose. The ring may be constructed from a non-radiopaque material. For example, the directional marker 400 is conformed to a portion of the ring and the ring is positioned over an outer diameter of the inner tubular member 210 during assembly, as described in greater detail herein.

The arc-shaped portion 410 can have a length 402 about a half, a third, or a quarter of the outer diameter of the inner tubular member 210 or any other suitable length. The arc-shaped portion 410 can have a width 404 of between approximately 0.005" and approximately 0.015", including values such as about 0.011". The extended portion 412 can extend from about the middle of the arc-shaped portion 410 forming a T-shape. The extended portion 412 can have any suitable width 406 or length 408. For example, the width 406 can be between approximately 0.1 mm and approximately 0.3 mm, including values such as about 0.2 mm, and the length 408 can be about 1 mm to about 1.2 mm.

FIG. 5 is a diagrammatic perspective view of a directional marker 500, according to aspects of the present disclosure. The directional marker 500 is a radiopaque marker similar to the directional markers 220a and 220c. The directional marker 500 is substantially similar to the directional marker 400, but has an L-shape instead of a T-shape. As shown, the directional marker 500 includes an arc-shaped portion 510 similar to the arc-shaped portion 410 and an extended portion 512 similar to the extended portion 412 extending from an end 502 of the arc-shaped portion 510 forming the L-shape. In an embodiment, similar to the directional marker 400, the directional marker 500 can be affixed to a ring for assembly purpose.

FIG. 6 is a diagrammatic top view of a directional marker 600, according to aspects of the present disclosure. The directional marker 600 is substantially similar to the directional markers 220, 400, and 500, but has a full circle portion 610 instead of a half circle. The directional marker 600 includes the full circle portion 610 and an extended portion 612 extending from the full circle portion 610. When the directional marker 600 is positioned on the intraluminal device 200, the full circle portion 610 wraps around an outer diameter of the inner tubular member 210 and the extended portion 612 extends along an outer surface of the inner tubular member 210.

While the directional markers 400, 500, 600 illustrated in FIGS. 4, 5, and 6 have a T-shape or an L-shape, the directional markers 400, 500, and 600 can be alternatively configured to achieve similar functionalities. For example, the extended portion 412, 512, or 612 can be extended at an angle from the arc-shaped portion 410, 510, or the full circle portion 610, respectively, instead of perpendicular.

Figure 7:
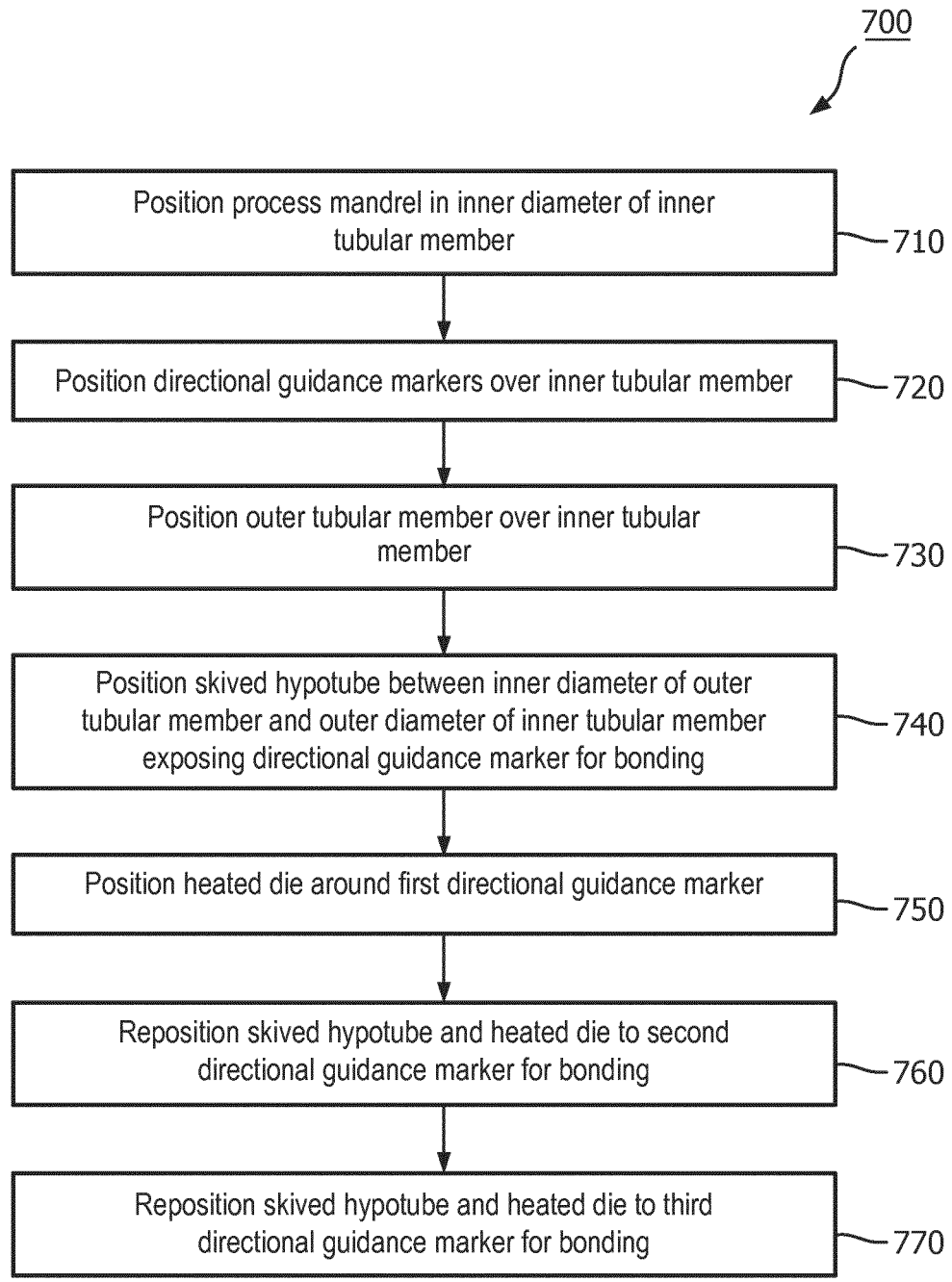
FIG. 7 is a flow diagram of a method of assembling an intraluminal with directional markers, according to aspects of the disclosure.
Figure 8:
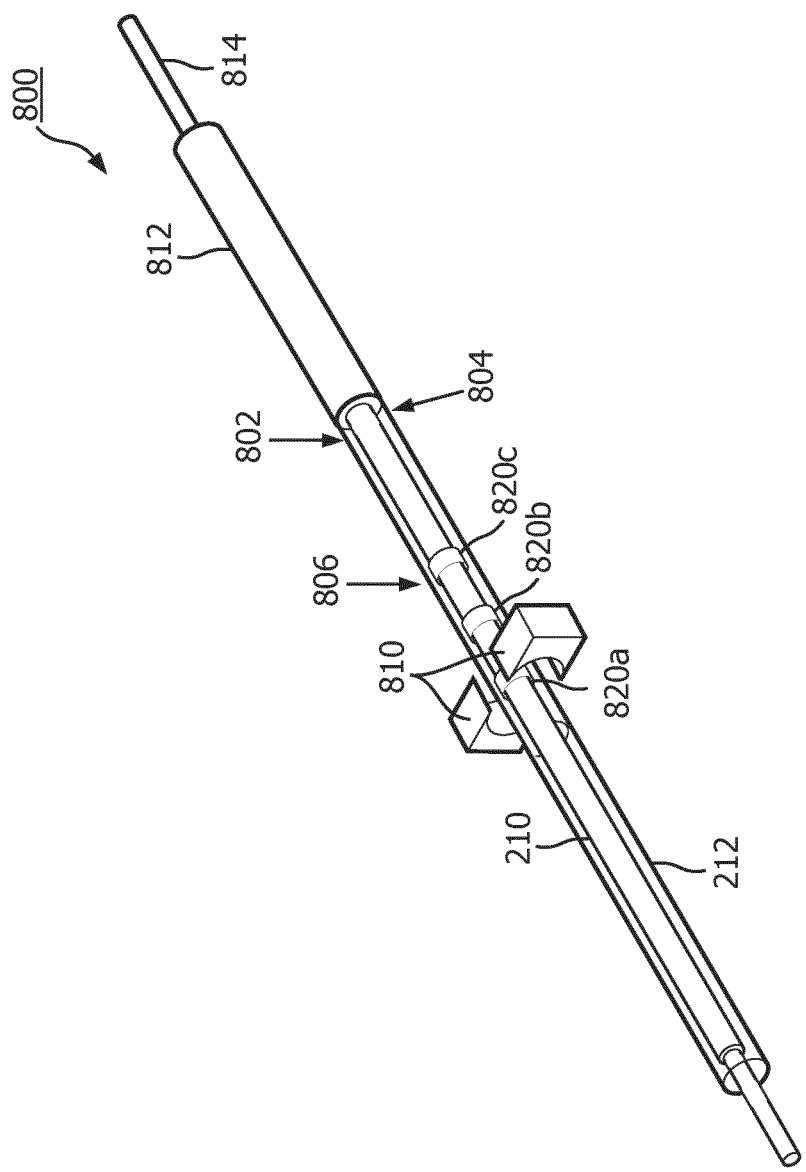
FIG. 8 is a diagrammatic perspective view of an intraluminal assembly with a first directional marker positioned for thermal bonding during a stage of manufacturing, according to aspects of the present disclosure.
Figure 9:
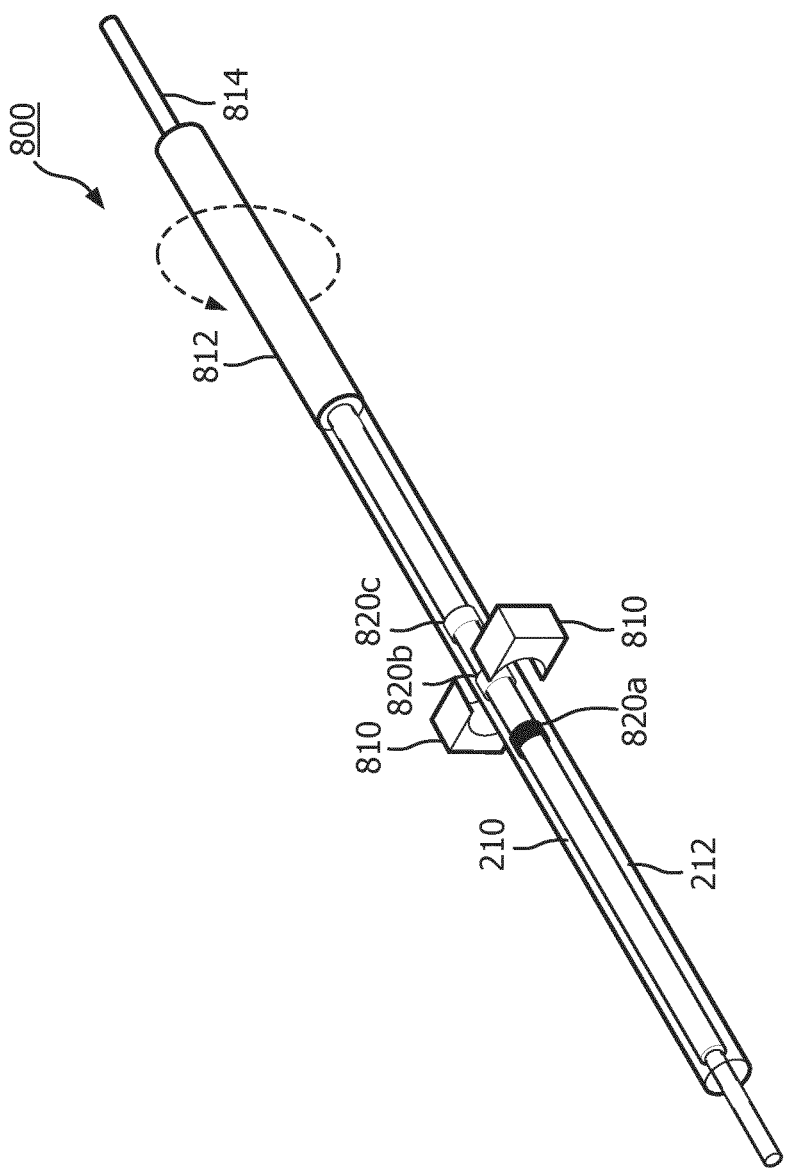
FIG. 9 is a diagrammatic perspective view of an intraluminal assembly with a second directional marker positioned for thermal bonding during a stage of manufacturing, according to aspects of the present disclosure.
Figure 10:
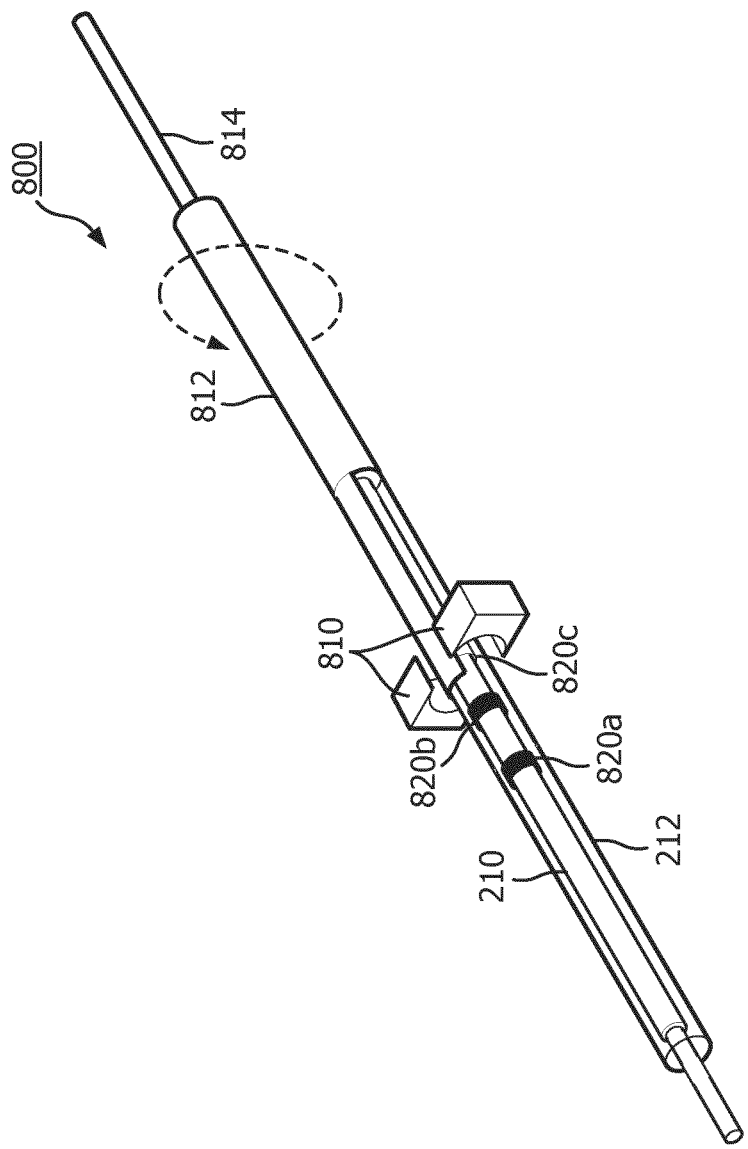
FIG. 10 is a diagrammatic perspective view of an intraluminal assembly with a third directional marker positioned for thermal bonding during a stage of manufacturing, according to aspects of the present disclosure.
Figure 11:
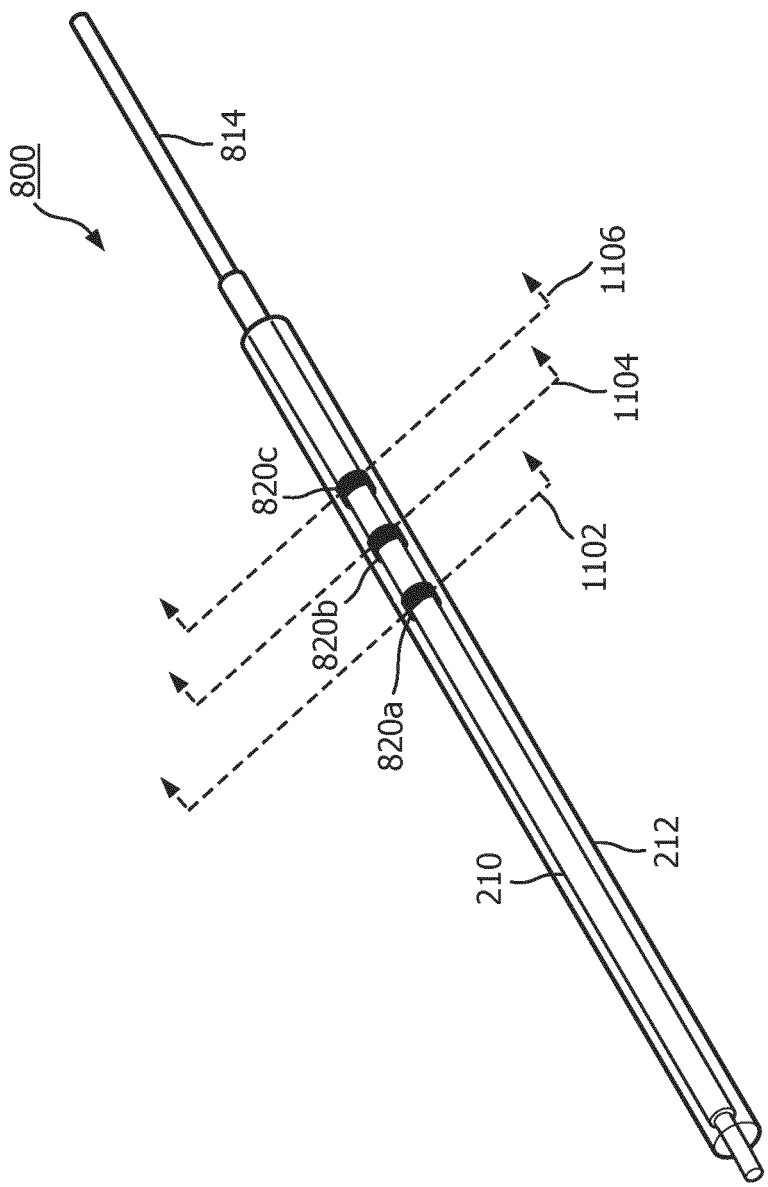
FIG. 11 is a diagrammatic perspective view of an intraluminal assembly with thermally bonded directional markers, according to aspects of the present disclosure.

A method 700 of assembling an intraluminal device such as the intraluminal device 200 with a series of individual directional markers 820 using tackweld process is described with reference made to FIGS. 7-11. FIG. 7 is a flow diagram of a method 700 of assembling an intraluminal device with directional markers, according to aspects of the disclosure. It is understood that additional steps can be provided before, during, and after the steps of method 700, and some of the steps described can be replaced or eliminated for other embodiments of the method. The steps of the method 700 can be carried out by a manufacturer of an intraluminal device. FIG. 8 is a diagrammatic perspective view of an intraluminal assembly 800 with a first directional marker 820a positioned for thermal bonding during a stage of manufacturing, according to aspects of the present disclosure. FIG. 9 is a diagrammatic perspective view of the intraluminal assembly 800 with a second directional marker 820b positioned for thermal bonding during a stage of manufacturing, according to aspects of the present disclosure. FIG. 10 is a diagrammatic perspective view of the intraluminal assembly 800 with a third directional marker 820c positioned for thermal bonding during a stage of manufacturing, according to aspects of the present disclosure. FIG. 11 is a diagrammatic perspective view of the intraluminal assembly 800 with the thermally bonded directional markers 820a, 820b, and 820c, according to aspects of the present disclosure.

Referring to the step 710 of the method 700 and FIG. 8, in an embodiment, a process mandrel 814 is positioned in the inner diameter of the inner tubular member 210.

Referring to the step 720 of the method 700 and FIG. 8, in an embodiment, the directional markers 820a, 820b, and 820c are positioned over the outer diameter of the inner tubular member 210. The directional markers 820 are substantially similar to the directional markers 220, 400, 500, and 600. For example, the directional markers 820 are constructed from tungsten. The directional markers 820a, 820b, and 820c can be positioned at a suitable distance from each other. In an embodiment, an adhesive can be applied to the directional markers 820a, 820b, and 820c to secure the positions of the directional markers 820a, 820b, and 820c to the inner tubular member 210.

Referring to the step 730 of the method 700 and FIG. 8, in an embodiment, the outer tubular member 212 is positioned over the inner tubular member 210, where the directional markers 820a, 820b, and 820c are positioned between the outer wall of the inner tubular member 210 and the inner wall of the outer tubular member 212.

Referring to the step 740 of the method 700 and FIG. 8, in an embodiment, a skived hypotube 812 is positioned between an inner diameter of the outer tubular member 212 and an outer diameter of the inner tubular member 210. The hypotube 812 has a notch 802 and a bottom portion 804. The notch 802 exposes a top side 806 of the assembly 800 (e.g., the directional markers 820). The bottom portion 804 prevents an opposite bottom side of the assembly 800 (e.g., the inner tubular member 210 and the outer tubular member 212) from fusing together (e.g., leaving a gap) during subsequent heating. The gap between inner tubular member 210 and the outer tubular member 212 provides access for an electrical cable (e.g. the electrical cable 112) to extend along the entire body of the assembly 800 during subsequent assembly.

Referring to the step 750 of the method 700 and FIG. 8, in an embodiment, a heated die 810 is positioned around the first directional marker 820a to thermally bond or fuse the top side 806 of the first directional marker 820a to an outer wall of the inner tubular member 210 and/or an inner wall of the outer tubular member 212. The bottom portion 804 of the skived hypotube 812 protects the bottom side of the assembly 800 from the heat.

Referring to the step 760 of the method 700 and FIG. 9, after the bonding of the directional marker 820a has completed, the skived hypotube 812 is repositioned to the second directional marker 820b. For example, the skived hypotube 812 can be rotated at an angle as shown by the dashed arrow such that the second directional marker 820b can have a length offset from the first directional marker 820a as shown in FIG. 9. The heated die 810 is repositioned to the second directional marker 820b to thermally bond a side of the second directional marker 820b to the outer wall of the inner tubular member 210 and/or the inner wall of the outer tubular member 212.

Referring to the step 770 of the method 700 and FIG. 10, after the bonding of the second directional marker 820b has completed, the skived hypotube 812 is repositioned to the third directional marker 820c. For example, the skived hypotube 812 is further rotated at an angle as shown by the dashed arrow so that the third directional marker 820c can have a length offset from the first directional marker 820a and the second directional marker 820b as shown in FIG. 10. The heated die 810 is repositioned to the third directional marker 820c to thermally bond a side of the third directional marker 820c to the outer wall of the inner tubular member 210 and/or the inner wall of the outer tubular member 212. The intraluminal assembly 800 with the thermally bonded directional markers 820 is shown in FIG. 11. As can be seen, the lengths of the directional markers 820 are offset from each other along the circumferences of the assembly 800.

Figure 12:
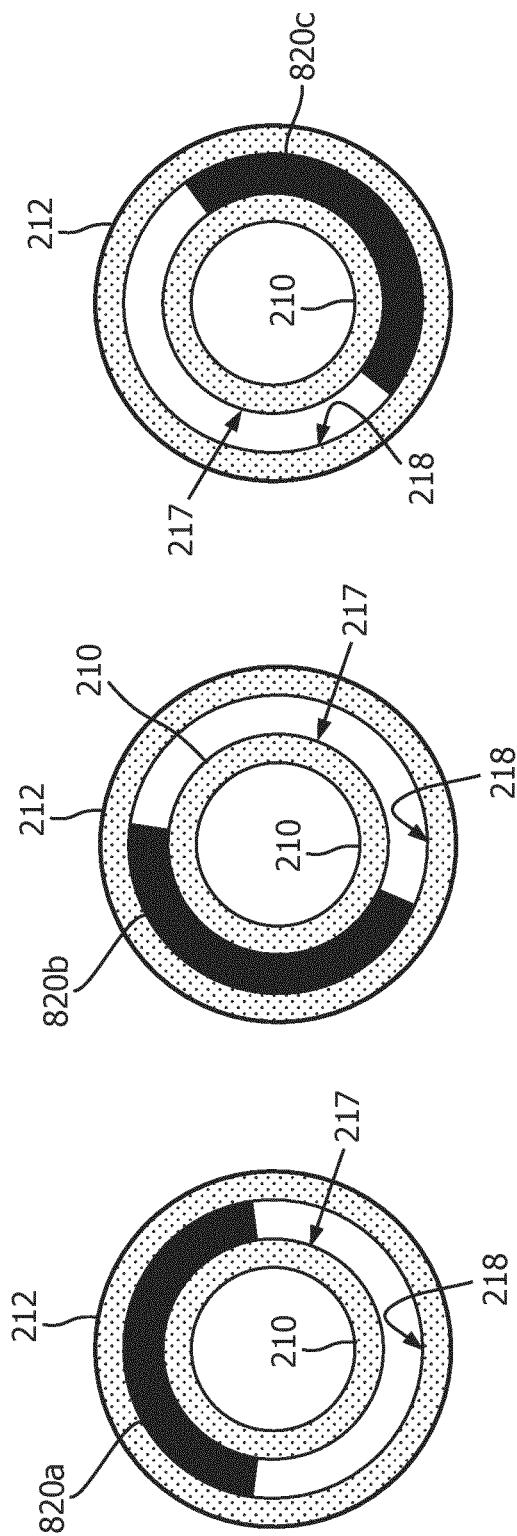
FIG. 12A is a diagrammatic cross-sectional view of an intraluminal assembly with a thermally bonded directional marker, according to aspects of the present disclosure.
FIG. 12B is a diagrammatic cross-sectional view of an intraluminal assembly with a thermally bonded directional marker, according to aspects of the present disclosure.
FIG. 12C is a diagrammatic cross-sectional view of an intraluminal assembly with a thermally bonded directional marker, according to aspects of the present disclosure.

FIGS. 12A, 12B, and 12C illustrate cross-sectional views of the directional markers 820 thermally bonded to the intraluminal assembly 800. FIG. 12A is a diagrammatic cross-sectional view of the intraluminal assembly 800 with the thermally bonded directional marker 820a taken along the line 1102 of FIG. 11, according to aspects of the present disclosure. FIG. 12B is a diagrammatic cross-sectional view of the intraluminal assembly 800 with the thermally bonded directional marker 820b taken along the line 1104 of FIG. 11, according to aspects of the present disclosure. FIG. 12C is a diagrammatic cross-sectional view of the intraluminal assembly 800 with the thermally bonded directional marker 820c taken along the line of 1106 of FIG. 11, according to aspects of the present disclosure. As shown, each of the directional markers 820a, 820b, and 820c is positioned between an outer wall 217 of the inner tubular member 210 and an inner wall 218 of the outer tubular member 212. As can be seen, the directional 820a, 820b, and 820c are offset from each other along the circumference of the inner tubular member 210 and the outer tubular member 212 and provide 3 different arrangement patterns offset by about 120 degrees when the intraluminal assembly 800 is viewed axially. In an embodiment, each of the directional markers 820 can additionally include an extended portion similar to the extended portions 412, 512, and 612. In such an embodiment, the directional markers 820 can be arranged such that the extended portions are also offset from each other, for example, to provide 6 different arrangement patterns offset by about 60 degrees. In some other embodiments, more direction markers similar to the 820 can be used to provide a finer angular directional granularity.

In some embodiment, directional markers such as the directional markers 220, 400, 500, 600, and 820 can be constructed from about 90 percent (%) of platinum and about 10% of iridium. In such embodiments, the directional markers can be swaged onto the inner tubular member 210. For example, a process mandrel (e.g., the process mandrel 814) can be positioned in the lumen of an inner tubular member (e.g., the inner tubular member 210) and the directional markers can be arranged to create different patterns with respect to different orientations of the imaging component 214 and swaged onto the outer wall of the inner tubular member 210. Subsequently, the outer tubular member 212 can be positioned over the inner tubular member 210 such that the directional markers are positioned between the inner wall (e.g., the inner wall 218) of the outer tubular member 212 and the outer wall (e.g., the outer wall 217) of the inner tubular member 210.

Figure 13:
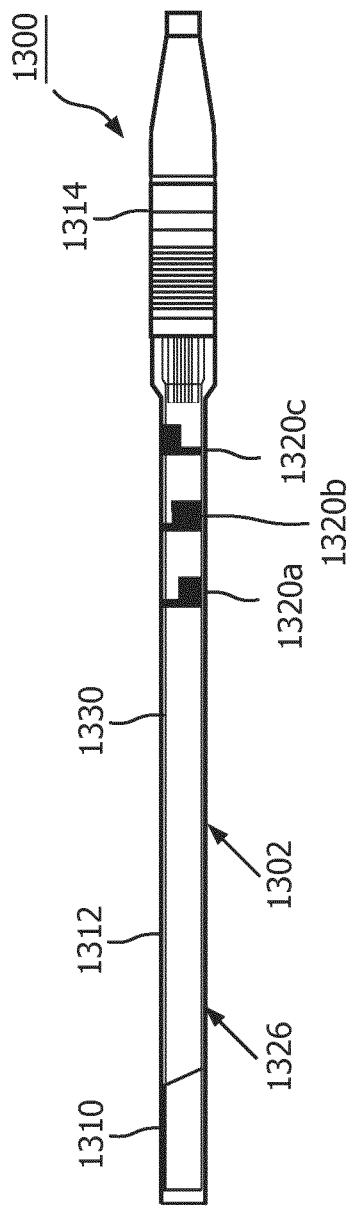
FIG. 13 is a diagrammatic perspective view of an intraluminal device with directional marker coils, according to aspects of the present disclosure.
Figure 14:
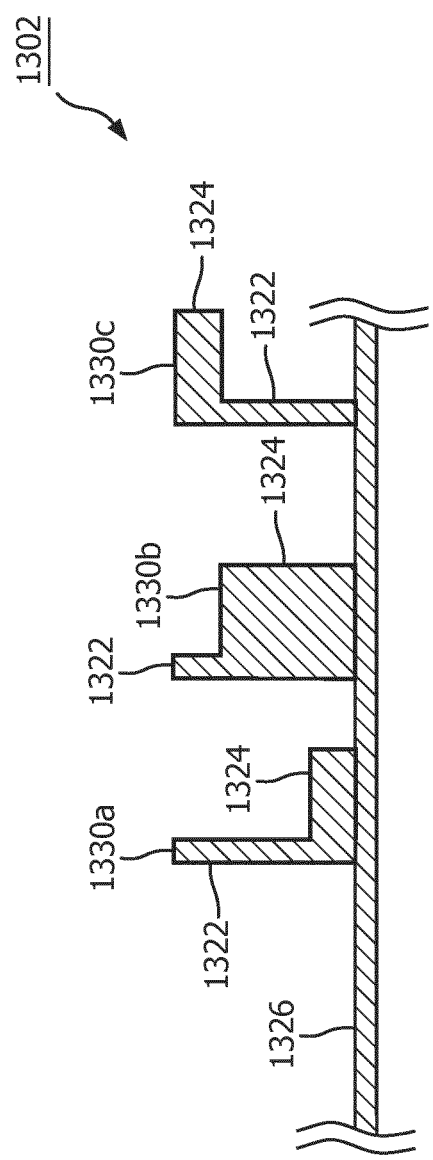
FIG. 14 is a diagrammatic side view of a portion of a directional marker coil assembly, according to aspects of the present disclosure.

FIGS. 13 and 14 illustrate additional directional marker assemblies to provide directional guidance on intraluminal devices such as the intraluminal devices 102 and 200 instead of or in addition to the directional markers 220, 400, 500, 600, and 820. FIG. 13 is a diagrammatic perspective view of an intraluminal device 1300 with directional marker markers 1320, according to aspects of the present disclosure. FIG. 14 is a diagrammatic side view of a portion of a directional marker assembly 1302, according to aspects of the present disclosure. The intraluminal device 300 is substantially similar to the intraluminal devices 102 and 200 and can be used in the system 100 in place of the intraluminal device 102. The intraluminal device 1300 includes a flexible elongate member 1330 similar to the flexible elongate member 230, an imaging component 1314 similar to the imaging component 214, and the directional marker assembly 1302. The directional marker assembly 1302 includes the directional markers 1320 attached to a flexible element or wire 1326. The directional markers 1320 are composed of a radiopaque material and can have similar geometries as the directional markers 220, 400, 500, 600, and 820 described with respect to FIGS. 2, 4, 5, 6, and 8, respectively, for providing directional guidance. As shown, each directional markers 1320a, 1320b, 1320c has an arc-shaped portion 1322 and an extended portion 1324 extending from the arc-shaped portion 1322. In some embodiments, the directional markers 1320a, 1320b, 1320c can be radiopaque coils. For example, the directional markers 1320a, 1320b, 1320c can be formed of windings of a wire for a radiopaque material. Tightly wound sections of the wire can be radiopaque and form the directional markers 1320a, 1320b, 1320c.

In an embodiment, the directional markers 1320 can be pre-configured in an L-shape or a T-shape and spaced apart by a suitable distance and attached to the flexible wire 1326. For example, the flexible wire 1326 may correspond to a loosely wound segment of a wire and the directional markers 1320 correspond to tightly wound segments of the wire with the radiopaque material. The flexible wire 1326 with the directional markers 1320 can be positioned between an outer wall of the inner tubular member 1310 and an inner wall of the outer tubular member 1312 and bonded by an adhesive.

Figure 15A:
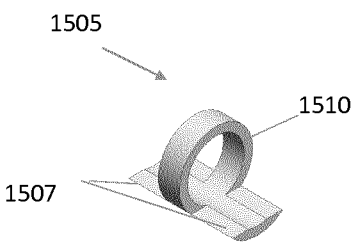
FIGS. 15A-15F include various embodiments of directional markers, according to aspects of the present disclosure.
Figure 15B:
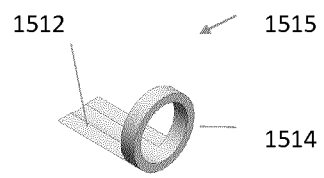
Figure 15C:
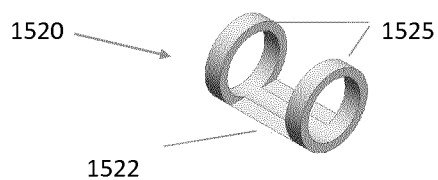
Figure 15D:
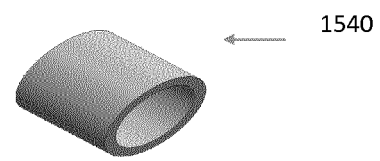
Figure 15E:
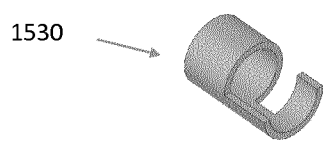
Figure 15F:
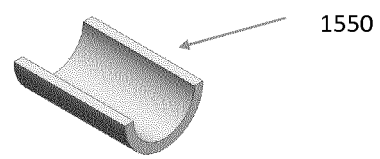

FIG. 15A-15F show additional shapes suitable for use as one or more of the directional markers in any one or combination of the above embodiments. FIG. 15A illustrates a directional marker 1505 that includes a ring member 1510, which may surround a body of the intraluminal device. The ring member 1510 is sandwiched between tabs 1507. As shown, the tabs 1507 are aligned, but they could also be staggered about the ring member 1510 with respect to each other. FIG. 15B illustrates directional marker 1515 with ring member 1514 having one or more tabs 1512 extending in one direction (distal or proximal) from the ring member. FIG. 15C illustrates a directional marker 1520 that includes a center elongate member 1522 sandwiched between tow ring members 1525. The center elongate member 1522 may be straight or curved in shape to conform to the shape of the intraluminal device. FIG. 15D illustrates a directional marker 1540 that is parallelogram in its shape. FIG. 15E illustrates a directional marker 1530 that is asymmetrical in its shape. The asymmetry may be across the longitudinal axis, latitudinal axis, or both. FIG. 15F illustrates a directional marker 1550 configured to only partial extend along a perimeter or circumference of a body of the intraluminal deice. As shown, the directional marker 1550 is shaped like a cuff.

Figure 16:
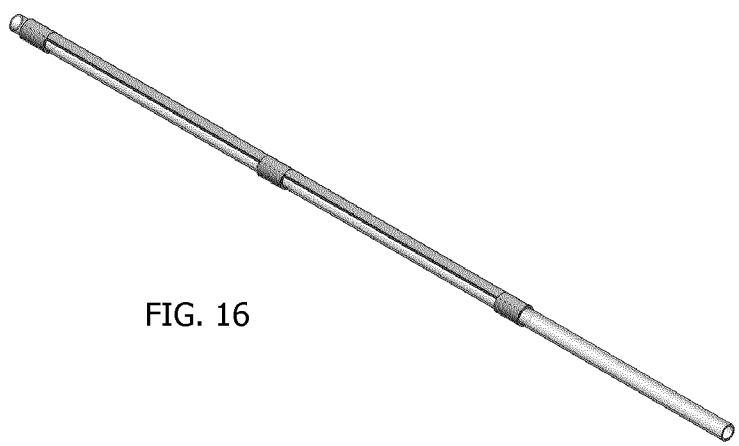
FIG. 16 illustrate an additional embodiment of directional markers, according to aspects of the present disclosure.

In some instance, one or more of the directional markers described here are connected by a radiopaque strip, as exemplified in FIG. 16

As discussed, many different materials may be used to create the directional markers of the invention, including— e.g., tungsten, platinum, iridium, and blends thereof. In some instances, a polymeric material may be doped to form directional markers of the invention. For example, the doped polymeric material may form or at least partially any one of the shapes described previously, in which all or only a portion of the shape is doped with a radiopaque material. In other instances, traditional components of the intraluminal device, e.g., shaft, tip, unibody, may be doped with a radiopaque material and used for the directional marker.

Aspects of the present disclosure can provide several benefits. For example, the staggering of the different shaped and/or sized radiopaque markers can provide different axial views at different axial angles, and thus may allow a clinician to determine an axial positioning of the intraluminal device, for example, the distance and/or angle, relative to a target site. As such, the disclosed embodiments can increase the accuracy of medical treatment procedures when used conjunction with IVUS transducers. For example, the specific patterns of the directional markers can provide directional guidance as to the length, orientation, and/or cutting distance relative to an atherosclerotic plaque during atherectomy or aid in directing thrombus removal. The disclosed embodiments are suitable for use in any clinical application requiring precise therapeutic directions. In addition, the employment of separate individual directional markers forming the specific patterns can provide axial positioning information without impacting the flexibility or navigational ability of the intraluminal device when accessing tortuous regions.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraluminal device comprising:
  a flexible elongate member including a proximal portion and a distal portion;
  an imaging component coupled to the distal portion of the flexible elongate member; and
  a first radiopaque marker and a second radiopaque marker positioned at the distal portion of the flexible elongate member,
  wherein the first radiopaque marker and the second radiopaque marker are separated from each other,
  wherein each of the first radiopaque marker and the second radiopaque marker includes:
    a first segment extending around only part of a circumference of the flexible elongate member, the first segment comprising a first end, a second end, and a first length extending between the first end and the second end; and
    a second segment extending longitudinally from the first segment and around only a part of the circumference of the flexible elongate member, the second segment comprising a second length smaller than the first length, wherein the second segment is connected only to the first segment and the flexible elongate member,
  wherein the first radiopaque marker and the second radiopaque marker:
    comprise a different structure than one another; and
    are positioned proximate to one another along a length of the flexible elongate member at the distal portion of the flexible elongate member,
  wherein the different structure than one another comprises:
    in the first radiopaque marker, the second segment extends longitudinally from a center of the first segment; and
    in the second radiopaque marker, the second segment extends longitudinally from the first end of the first segment,
    such that the second segment of the first radiopaque marker and the second segment of the second radiopaque marker are offset from one another,
  wherein the first segment of the first radiopaque marker is aligned with the first segment of the second radiopaque marker such that
    the first end in the first radiopaque marker is aligned with the first end in the second radiopaque marker; and
    the second end in the first radiopaque marker is aligned with the second end in the second radiopaque marker.

2. The intraluminal device of claim 1, wherein the first radiopaque marker and the second radiopaque marker include at least one of a tungsten material, platinum, or iridium.

3. The intraluminal device of claim 1, wherein the first radiopaque marker and the second radiopaque marker comprise a plurality of radiopaque coils.

4. The intraluminal device of claim 1, wherein each of the first radiopaque marker and the second radiopaque marker comprises only one second segment.

5. The intraluminal device of claim 1,
  wherein the flexible elongate member includes an inner tubular member and an outer tubular member extending between the proximal portion and the distal portion, and
  wherein the first radiopaque marker and the second radiopaque marker are positioned between the inner tubular member and the outer tubular member at the distal portion.

6. The intraluminal device of claim 5,
  wherein the first segment of at least one of the first radiopaque marker or the second radiopaque marker is positioned around a portion of an outer diameter of the inner tubular member, and
  wherein the second segment of the at least one of the first radiopaque marker or the second radiopaque marker extends along an outer wall of the inner tubular member.

7. The intraluminal device of claim 5, wherein at least portions of the first radiopaque marker and the second radiopaque marker are thermally bonded to at least an outer wall of the inner tubular member.

8. The intraluminal device of claim 5, wherein at least portions of the first radiopaque marker and the second radiopaque marker are thermally bonded to an outer wall of the inner tubular member and an inner wall of the outer tubular member.

9. The intraluminal device of claim 5, wherein the first radiopaque marker and the second radiopaque marker are swaged onto at least an outer wall of the inner tubular member by an adhesive.

10. The intraluminal device of claim 5, wherein the first radiopaque marker and the second radiopaque marker are bonded to at least an outer wall of the inner tubular member by an adhesive.

11. The intraluminal device of claim 5, further comprising a flexible element extending along the flexible elongate member such that the flexible element is distinct from the flexible elongate member, wherein the first radiopaque marker and the second radiopaque marker are attached to the flexible element.

12. The intraluminal device of claim 11, wherein the flexible element is a wire extending along a length between the inner tubular member and the outer tubular member.

* * * * *